US008007823B2

(12) United States Patent
Favis et al.

(10) Patent No.: US 8,007,823 B2
(45) Date of Patent: Aug. 30, 2011

(54) MICROPOROUS ARTICLES COMPRISING BIODEGRADABLE MEDICAL POLYMERS, METHOD OF PREPARATION THEREOF AND METHOD OF USE THEREOF

(75) Inventors: Basil D. Favis, Kirkland (CA); Pierre Sarazin, Montreal (CA); Jianming Li, Montreal (CA); Zhenhua Yuan, Montreal (CA)

(73) Assignee: Corporation de l'Ecole Polytechnique de Montreal, Montreal (CA)

( * ) Notice: Subject to any disclaimer, the term of this patent is extended or adjusted under 35 U.S.C. 154(b) by 1051 days.

(21) Appl. No.: 10/552,357

(22) PCT Filed: Apr. 2, 2004

(86) PCT No.: PCT/CA2004/000500
§ 371 (c)(1),
(2), (4) Date: Jul. 13, 2006

(87) PCT Pub. No.: WO2004/087797
PCT Pub. Date: Oct. 14, 2004

(65) Prior Publication Data
US 2007/0116737 A1     May 24, 2007

Related U.S. Application Data

(60) Provisional application No. 60/459,635, filed on Apr. 3, 2003.

(51) Int. Cl.
*A61F 2/00* (2006.01)
(52) U.S. Cl. ............ 424/426; 521/50; 521/61; 424/423; 623/1.38; 623/1.39

(58) Field of Classification Search ............ None
See application file for complete search history.

(56) References Cited

U.S. PATENT DOCUMENTS

| 4,186,448 A | 2/1980 | Brekke |
| 4,702,917 A | 10/1987 | Schindler |

(Continued)

FOREIGN PATENT DOCUMENTS

EP     0 246 752 A2     11/1987

(Continued)

OTHER PUBLICATIONS

Washburn, N.R. et al., Journal of Biomedical Materials Research, 2002, vol. 60, No. 1, pp. 20-29.

*Primary Examiner* — Robert A Wax
*Assistant Examiner* — Bethany Barham
(74) *Attorney, Agent, or Firm* — Goudreau Gage Dubuc; Alain A. M. Leclerc

(57) ABSTRACT

The present invention relates to a highly controlled method of preparation of a microporous biodegradable polymeric article. Firstly, at least one biodegradable polymer A, one polymer B, biodegradable or not, partially or totally immiscible with A, and a compatibilizer C for A and B are selected. Secondly, the selected polymers are melt-blended, thereby preparing a polymer blend, wherein said polymers A and B have an essentially continuous morphology. Thirdly, after cooling, polymer B and compatibilizer C are selectively extracted from the polymer blend by dissolution in a solvent that is a non-solvent of polymer A. The resulting polymeric article has an essentially continuous porosity with a void volume between 10 and 90% and a unimodal diameter distribution set to a predefined unimodal peak location. It can be used in tissue engineering, for controlled release applications or as an implantable medical device.

43 Claims, 16 Drawing Sheets

U.S. PATENT DOCUMENTS

| | | | |
|---|---|---|---|
| 4,721,732 A | 1/1988 | Dubrow et al. | |
| 4,822,678 A * | 4/1989 | Brody et al. | 428/373 |
| 4,859,715 A | 8/1989 | Dubrow et al. | |
| 5,102,983 A | 4/1992 | Kennedy | |
| 5,133,755 A | 7/1992 | Brekke | |
| 5,290,494 A | 3/1994 | Coombes et al. | |
| 5,492,697 A | 2/1996 | Boyan et al. | |
| 5,502,092 A | 3/1996 | Barrows et al. | |
| 5,514,378 A | 5/1996 | Mikos et al. | |
| 5,522,895 A | 6/1996 | Mikos | |
| 5,567,612 A | 10/1996 | Vacanti et al. | |
| 5,607,474 A | 3/1997 | Athanasiou et al. | |
| 5,677,355 A | 10/1997 | Shalaby et al. | |
| 5,686,091 A | 11/1997 | Leong et al. | |
| 5,711,960 A | 1/1998 | Shikinami | |
| 5,716,413 A | 2/1998 | Walter et al. | |
| 5,723,508 A | 3/1998 | Healy et al. | |
| 5,755,792 A | 5/1998 | Brekke | |
| 5,769,899 A | 6/1998 | Schwartz et al. | |
| 5,770,193 A | 6/1998 | Vacanti et al. | |
| 5,856,367 A | 1/1999 | Barrows et al. | |
| 5,863,297 A | 1/1999 | Walter et al. | |
| 5,866,155 A | 2/1999 | Laurencin et al. | |
| 5,869,080 A | 2/1999 | McGregor et al. | |
| 5,969,020 A | 10/1999 | Shalaby et al. | |
| 6,013,853 A | 1/2000 | Athanasiou et al. | |
| 6,103,255 A | 8/2000 | Levene et al. | |
| 6,203,573 B1 | 3/2001 | Walter et al. | |
| 6,245,345 B1 | 6/2001 | Swanbom et al. | |
| 6,281,256 B1 | 8/2001 | Harris et al. | |
| 6,281,257 B1 * | 8/2001 | Ma et al. | 521/61 |
| 6,333,029 B1 | 12/2001 | Vyakarnam et al. | |
| 6,334,968 B1 | 1/2002 | Shapiro et al. | |
| 6,337,198 B1 | 1/2002 | Levene et al. | |
| 6,355,699 B1 | 3/2002 | Vyakarnam et al. | |
| 6,365,149 B2 | 4/2002 | Vyakarnam et al. | |
| 6,511,511 B1 * | 1/2003 | Slivka et al. | 623/23.75 |
| 2002/0005600 A1 * | 1/2002 | Ma | 264/49 |
| 2002/0102674 A1 | 8/2002 | Anderson | |

FOREIGN PATENT DOCUMENTS

EP     0 283 187 A2     9/1988

\* cited by examiner a)　　　　　　　　　　b)　　　　　　　　　　c)

MICROPOROUS ARTICLES COMPRISING BIODEGRADABLE MEDICAL POLYMERS, METHOD OF PREPARATION THEREOF AND METHOD OF USE THEREOF

CROSS REFERENCE TO RELATED APPLICATIONS

This application represents the U.S. National Stage under 35 USC §371 of International Application PCT/CA2004/000500, filed Apr. 2, 2004, which was published in English, designated/elected the United States of America, and claimed priority to U.S. Provisional application 60/459,635, filed Apr. 3, 2003, both of which are incorporated into the present application in their entirety for all purposes.

FIELD OF THE INVENTION

The present invention relates to microporous articles comprising biodegradable medical polymers and to methods of making and using these articles.

BACKGROUND OF THE INVENTION

Porous polymeric biomaterials and implants composed of biodegradable polymers have been presented in numerous papers and patents. These biomaterials and implants are generally made of aliphatic polyesters such as polylactic acids) and polylactides [PLAs], poly(glycolic acids) and polyglycolides [PGAs], poly(lactic-co-glycolic) and poly(lactide-co-glycolide) [PLGA], polyglyconate, poly(hydroxyalkanoates) [PHAs], polyorthoesters [POEs], polycaprolactones [PCLs], polydioxanone [PDS], polyanhydrides [PANs], and their copolymers. The American Food and Drug Administration (FDA) has cleared medical devices made from homopolymers or copolymers of glycolide, lactide, caprolactone, p-dioxanone and trimethylene carbonate.

Porous polymeric biomaterials have been promoted as carriers or scaffolds for repairing tissues, delivering drugs and bioactive compounds, encapsulating cells or bioengineering artificial tissues. The repair or regeneration of bone, cartilage, skin, liver, etc have attracted interest in such biodegradable porous polymer materials.

A number of physico-chemical techniques have been proposed to build such porous polymer structures. Washburn et al. (*Co-extrusion of biocompatible polymers for scaffolds with co-continuous morphology*, New York, John Wiley and Sons, Inc. 2002) disclose an approach using the melt blending of two immiscible polymers, only one of which being soluble in water (or another solvent) and at least the other one of which being biodegradable. Melt blending takes place in a twin screw extruder and is followed by selective extraction of one of the polymers to generate a porous biodegradable material, having a continuous network of void spaces. This material is then used to carry out tissue engineering.

Although this paper briefly mentions some factors that control the morphology of the extruded material, for example the viscosity of each polymer, the interfacial tension between the phases and the mixing conditions, it remains completely silent about how to closely control said morphology by manipulating such factors. In one sample obtained according to the Washburn et al. technique, the pore size can vary from 20 to 150 micron in diameter from one end to the other of the void network. There is definitely a lack of pore size uniformity or distribution control in the continuous void network.

Besides, other techniques have also been used, a few examples of which are cited below, with the alternate drawbacks of leading either to a non-continuous void space or to a non-controlled continuous void network. Moreover, most of the prior art leads to the development of articles with dimensions and shapes limited by the process (film, membrane, and disk).

Biodegradable Microporous Polymer Materials Obtained Using Solid Porogens

Solid porogens, soluble in water or specific solvents, were used to develop polymer foams made of PLAs, PGAs or PLGA for tissue engineering. This particulate-leaching method consists in dispersing solid particles in a polymer solution, followed by the selective extraction of the particles. U.S. Pat. No. 5,522,895 (Mikos) and U.S. Pat. No. 5,514,378 to Mikos et al. describe such an approach to prepare porous polymer membranes by dispersing particles (salts or an organic or inorganic compound, proteins, polysaccharides) in a biocompatible polymer solution, leaching the polymer solvent, dissolving the particles and removing the solvent by evaporation to form a porous membrane. Three-dimensional structures are achieved by laminating a number of various membranes.

Biodegradable Microporous Polymer Materials Obtained by Phase Separation from Polymer Solutions Phase separation of polymer solutions was a straightforward porogen method for the production of polymer porous foams. This phase separation may be induced thermally (for example, by freeze-drying), by dry casting, by immersion precipitation, or by precipitation from the vapour phase. U.S. Pat. No. 5,102,983 (Kennedy) and U.S. Pat. No. 6,334,968 (Shapiro et al.) use a freeze-drying step. U.S. Pat. No. 5,866,155 (Laurencin et al.) provides methods for producing polymer microspheres using a dissolution/solvent evaporation technique. U.S. Pat. Nos. 5,716,413, 5,863,297, 6,203,573 (Walter, et al) and U.S. Pat. No. 5,607,474 (Athanasiou, et al) use precipitated polymer gel masses to produce a molded biodegradable, porous polymeric implant. U.S. Pat. No. 52,902,494 (Coombes et al.) and U.S. Pat. No. 5,492,697 (Boyan et al.) use gel casting. The gel is extracted with a non-solvent prior to drying, in order to obtain the microporous materials. U.S. Pat. Nos. 5,502,092 and 5,856,367 (Barrows et al.) use a polymer dissolved in a low molecular weight material or monomer, then remove the latter by leaching with a solvent which does not react undesirably with the polymer. U.S. Pat. Nos. 6,333,029, 6,355,699, 6,365,149 to Vyakarnam et al. describe the lyophilization process for forming biocompatible foam structures, by solidifying a solution of a solvent and a bioabsorbable polymer to form a solid, then subliming the solvent out of the solid.

U.S. Pat. No. 5,869,080 (McGregor et al.) uses a solution of polymer and adds particles of a second material (frozen water) and removes the solvent and the second material by freeze-drying to leave the porous implant material.

U.S. Pat. No. 5,686,091 (Leong, et al) discloses a method in which biodegradable porous polymer scaffolds are prepared by molding a solvent solution of the polymer under conditions permitting spinodal decomposition, followed by quenching of the polymer solution in the mold and sublimation of the solvent from the solution.

U.S. Pat. No. 5,723,508 (Healy et al.) discloses a method in which biodegradable porous polymer scaffolds are prepared by forming an emulsion of the polymer, a first solvent in which the polymer is soluble, and a second polymer that is immiscible with the first solvent, and then freeze-drying the emulsion under conditions that do not break the emulsion or throw the polymer out of solution.

U.S. Pat. Nos. 6,103,255 and 6,337,198 (Levene et al.) describe a method employing thermally induced phase separation to fabricate highly porous biodegradable materials. Depending upon the thermodynamics, the kinetics and the rate of cooling, phase separation will occur either by solvent crystallization or liquid-liquid demixing. This invention employs solvents and processing conditions under which solvent crystallization predominates as the phase separation mechanism to obtain a porous polymer scaffold with a bimodal pore diameter distribution.

U.S. Pat. No. 6,013,853 (Athanasiou et al.) relates to a method of making a biodegradable, porous, polymeric implant by a combination of dissolution/precipitation/drying and treatment with high vacuum.

Textile-Based Porous Materials

U.S. Pat. No. 4,186,448 (Brekke et al., 1980) describes the use of a porous meshwork of plugs composed of polyhydroxy acid polymers such as polylactide for healing bone voids. U.S. Pat. Nos. 5,755,792 and 5,133,755 (Brekke) present the use of vacuum foaming techniques and a process of forming connected spun filaments.

U.S. Pat. No. 6,245,345 (Swanbom et al.) describes a method to produce a filamentous porous mesh as biodegradable scaffold. U.S. Pat. No. 5,711,960 (Shikinami), U.S. Pat. Nos. 5,567,612 and 5,770,193 (Vacanti, et al), and U.S. Pat. No. 5,769,899 (Schwartz, et al) use a method to make biodegradable textile-based fibrous scaffolds.

Other Methods for Obtaining Biodegradable Microporous Materials

U.S. Pat. No. 6,281,256 (Harris et al.) describes the preparation of porous polymer materials by a combination of gas forming and particulate leaching steps. U.S. Pat. Nos. 5,677,355 and 5,969,020 (Shalaby et al.) use a polymer melt with a fugitive compound that sublimes at temperatures greater than room temperature or can be extracted, in order to produce microcellular foams.

None of the cited prior art documents disclose a precise control of the combined interconnectivity of the pores, void volume and pore size distribution. More specifically, the prior art fails to recognize the considerable effect of the use of a compatibilizer in a melt polymer blend for such purpose. The prior art also remains silent on any processing technique to prepare complex shapes of biodegradable, continuous, porous, polymer structures.

Thus remains a need for a technique allowing the control of the morphology, void volume and pore size distribution of the void volume in biodegradable porous articles.

Thus also remains a need for biodegradable articles having an essentially continuous porosity, controlled void volume and a unimodal pore size distribution set to a predefined unimodal peak location.

The present invention seeks to meet these and other needs.

The present description refers to a number of documents, the content of which is herein incorporated by reference in their entirety.

SUMMARY OF THE INVENTION

The present invention aims at controlling the morphology, void volume and pore size distribution of the void space in biodegradable microporous articles by manipulating some parameters in the preparation process.

The present invention relates to a novel method for obtaining improved, biodegradable microporous articles with highly controlled-morphology and void volume, from a co-continuous polymer blend.

The invention also relates to a biodegradable microporous article having an improved morphology over prior art articles, and to uses of such an article.

More specifically, the present invention relates to a method of preparation of a microporous biodegradable polymeric article, comprising the following steps a) selecting at least one biodegradable polymer A, one polymer B, biodegradable or not, at least partially immiscible with A, and a polymeric compatibilizer C for A and B;

b) melt blending the selected polymers from step a) and the compatibilizer C, thereby preparing a compatibilized polymer blend, wherein polymers A and B have an essentially continuous morphology;

c) cooling the polymer blend to room temperature, thereby retaining its morphology; and d) extracting polymer B and compatibilizer C, at least partially, from the polymer blend by dissolving them in a solvent that is a non-solvent of polymer A, wherein said polymeric article has an essentially continuous porosity with a void volume of 10-90%, wherein pore diameters show a unimodal pore size distribution set to a predefined unimodal peak location corresponding to a chosen pore diameter and wherein a majority of pores has a diameter within ±50% of the chosen pore diameter.

It also relates to a biodegradable microporous polymeric article having an essentially continuous porosity, a controlled void volume from 10 to 90% and a unimodal pore size distribution set to a predefined unimodal peak location corresponding to a chosen pore diameter, wherein a majority pores have a diameter within ±50% of the chosen pore diameter.

The advantages of the present invention are wide in scope and can be used to produce uniform symmetrical porous structures, asymmetric pore structures, open cell materials, and closed cell materials.

Other objects and further scope of applicability of the present invention will become apparent from the detailed non-restrictive description given hereinafter. It should be understood, however, that this detailed description, while indicating preferred embodiments of the invention, is given by way of illustration only, with reference to the accompanying drawings, since various changes and modifications within the spirit and scope of the invention will become apparent to those skilled in the art.

DETAILED DESCRIPTION OF ILLUSTRATIVE EMBODIMENTS

Figure 1:
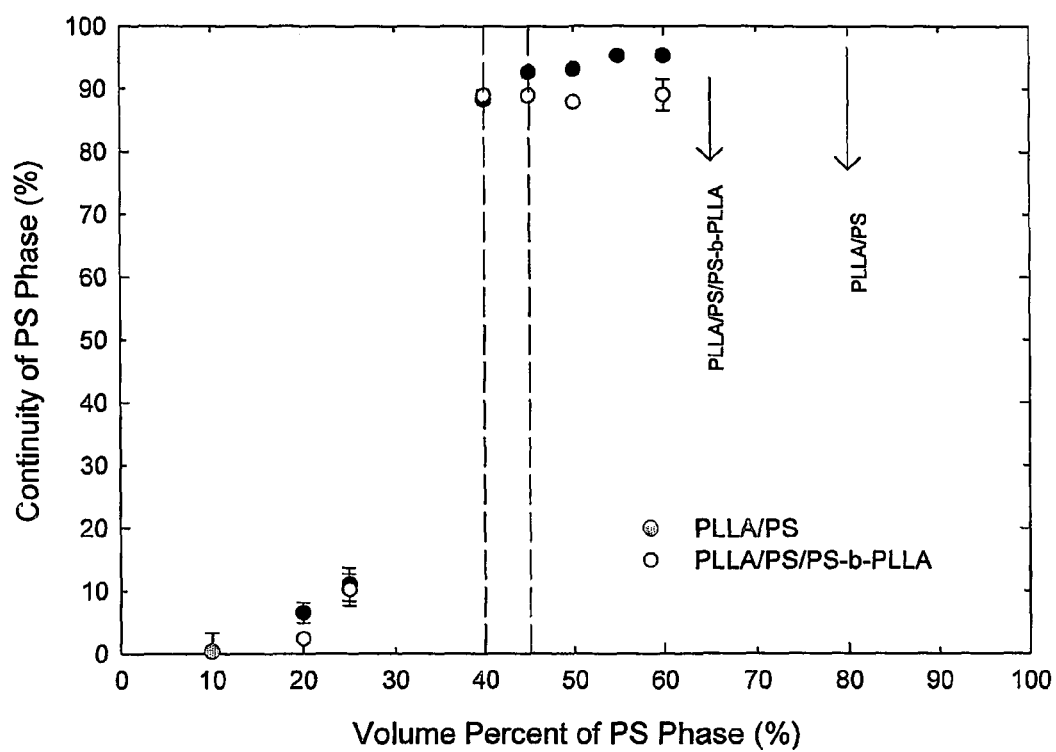
FIG. 1 is a diagram showing the continuity of the polystyrene phase as a function of PS volume fraction in the polymer blend; PPLA/PS blend and PPLA/PS/diblock blend are shown. The arrows indicate the point of disintegration of the samples.

Before describing the present invention in detail, it is to be understood that the invention is not limited in its application to the details of construction and parts illustrated in the accompanying drawings and described herein. The invention is capable of other embodiments and of being practiced in various ways. It is also to be understood that the phraseology or terminology used herein is for the purpose of description and not limitation.

In general terms, the present invention relates to a novel microporous biodegradable polymeric article comprising an essentially continuous porosity and a unimodal pore size distribution set to a predefined unimodal peak location and to its possible uses.

It also relates to a novel method of preparing microporous articles made of biodegradable medical polymers, for medical and surgical applications, comprising blend mixing of two or more polymers demonstrating at least partial immiscibility in the molten state with or without a compatibilizer, and selectively dissolving one of the phases.

This method allows the preparation of microporous articles with highly controlled pore size (diameter), pore volume (void volume) and pore size distribution, which can then be transformed and shaped in various forms useful for medical and surgical applications. Various properties of the skin of the polymeric articles (closed-cell, open-cell, modification of the pore size) can be controlled.

As used herein, an "article" refers to any formed or shaped material. The expression "polymeric article" refers to an article that is significantly composed of at least one polymer.

As used herein, the term "porous" refers to the property of a material of having pores, that is to say void spaces. The term "microporous" refers herein to such pores having an average diameter in the range of about 20 nm to about 500 µm. The term "porosity" refers herein to the void volume in a porous article. The "majority of pores" refers herein to at least 50% of the void volume in a porous article.

As used herein, the term "polymer blend" refers to a mixture of two or more polymers of different structure.

As used herein, the term "porogen phase" refers to the phase to be extracted out of the polymer blend, thereby creating the porosity of the final article.

As used herein when referring to polymer blends or to articles, the term "continuous" refers herein to one of the polymer phases or to the void space (pores), being essentially constituted of a three-dimensional network of interconnected domains. The term "co-continuous" refers to a blend wherein each polymer phase is continuous, essentially constituted of a network of interconnected domains.

As used herein, the expression "essentially continuous" means highly or fully continuous. The expression "highly continuous" refers herein to any three-dimensional networks that are greater than 50% continuous as determined by solvent extraction/gravimetry. The expression "fully continuous" refers herein to 100% continuous three-dimensional networks.

As used herein, the term "biodegradable" refers herein to the property of being broken down, chemically, physically or biologically, in a biological environment. In the medical field, natural physiological and metabolic pathways can eliminate the biodegradation products. As used herein, the term "biocompatible" is the ability of a material to elicit an appropriate biological response in a given biological application. This definition implies that any material placed into the body will not be inert and will interact with tissues in a dynamic way, altering both the material and the tissues around it.

As used herein, the term "morphology" refers to the internal and external structure of a polymer blend or article.

As used herein, the term "skin" refers to the part of a polymeric article close to its surface, as opposed to its remaining core. The expression "closed-cell" refers to the surface of the porous polymeric article that does not show any pore. The expression "open-cell" refers to the surface of the porous polymeric article, where the porosity is fully apparent.

A "symmetric morphology" refers herein to a porous structure that would be identical at the surface and in the core of the porous article. An "asymmetric morphology" refers herein to a porous structure that would differ at the surface as compared to the core of the porous article.

As used herein, a "compatibilizer" is a compound that reduces the interfacial tension between two immiscible polymers.

As used herein, the term "distribution" refers to a set of numbers (the pore sizes or pore diameters for example) and their frequency of occurrence, collected from measurements over a statistical population. A "unimodal distribution" is a distribution having a single local peak, called the Mode.

As used herein when referring to the pores of an article, the term "Number Average Diameter" (dn) refers to a value obtained with the following formula: $dn=(\Sigma n_i d_i)/(\Sigma n_i)$, wherein $n_i$ is the number of pores of diameter $d_i$. The expression "Volume Average Diameter" ($d_v$) refers to a value obtained with the following formula: $d_v=(\Sigma n_i d_i^4)/(\Sigma n_i d_i^3)$, wherein $n_i$ is the number of pores of diameter $d_i$. Such values can also be obtained experimentally.

Description of the Method for Preparing the Novel Porous Biodegradable Article:

In the present invention, the method of preparation of a microporous biodegradable polymeric article comprises the basic steps of:
a) selecting at least one biodegradable polymer A, one polymer B, biodegradable or not; at least partially immiscible with A, and a polymeric compatibilizer C for A and B,
b) melt blending the selected polymers from step a) and the compatibilizer C, thereby preparing a compatibilized polymer blend, wherein said polymers A and B have an essentially continuous morphology,
c) cooling the polymer blend to room temperature, thereby retaining its morphology, and
d) extracting polymer B and compatibilizer C, at least partially, from the polymer blend by dissolving them in a solvent that is a non-solvent of polymer A, wherein said polymeric article has an essentially continuous porosity with a void volume from 10 to 90%, wherein the pore diameters show a unimodal pore size distribution set to a predefined unimodal peak location corresponding to a chosen pore diameter, and wherein a majority of pores has a diameter within ±50% of the chosen pore diameter.

Selection and Physical Parameters of the Materials

The selection of polymer A determines the selection of polymer B, which is the porogen phase here, to be able to realize the above steps. At least one solvent should exist, in which B, and not A, is soluble. A and B should also be immiscible, at least partially. A Dynamic Mechanical Thermal Analysis (DMTA) can confirm their level of immiscibility. The selected polymers are known to be fully immiscible if the blend demonstrates clearly distinct Glass Transition Temperatures equivalent to the pure polymers. They are known to be partially immiscible if the blend demonstrates distinct Glass Transition Temperatures that have shifted towards each other. Apart from those two conditions, the choice of B is actually unlimited since it is to be extracted out. A number of variables can therefore be used to control the structure of the network: the interfacial tension of the binary blend, the temperature, the composition, the viscosity and elasticity of the blend components, the interfacial modification, the level of continuity and the annealing conditions, for example.

It is also possible to chose more than one polymer A and/or B for the purpose of this invention.

The selection of the polymers A and B then determines the composition range to obtain a co-continuous morphology of the blend. It is known that an immiscible binary polymer blend usually results in a morphology showing a dispersed phase of the minor polymer located within the matrix of the major polymer. Increasing the concentration of the minor phase eventually leads to phase inversion at which point the dispersed phase becomes the matrix and vice-versa. Near the phase inversion composition, each phase can be fully interconnected through a continuous pathway. This particular morphological state of a polymer blend is called co-continuity.

In a preferred embodiment, the compatibilizer used is a block or graft copolymer of A and B. It is added as a discrete third component, to modify the interface between the immiscible polymers. It is melt blended with A and B and at least partially extracted with B. Such an addition corresponds to what is called herein a "compatibilization" of the immiscible blend polymers. It essentially results in reducing the phase size and narrowing the phase-size distribution. This reduction in phase size is related to both a decrease in interfacial tension and reduced coalescence.

In the present invention, additives can also be incorporated within the polymer blend system. Additives used are generally non-polymeric, and may comprise at least one organic stabilizer for polymer A or B or for the polymer blend system.

In the present invention, polymer A is a biodegradable medical polymer, and preferentially an aliphatic polyester [poly(hydroxy acids)]. Polymer A can be selected among poly(lactic acid), poly(glycolic acid), poly(lactic-co-glycolic), poly(hydroxyalkanoates), poly-orthoesters, polycaprolactones, polydioxanone, polyanhydrides, and their copolymers.

In a particular embodiment of the present invention, polymer B is a non-biodegradable polymer. In a preferred embodiment, B is a biodegradable medical polymer selected in a group consisting of poly(lactic acid), poly(glycolic acid), poly(lactic-co-glycolic), poly(hydroxyalkanoates), poly-orthoesters, polycaprolactones, polydioxanone, polyanhydrides, and their copolymers. The advantage of choosing B as a biodegradable polymer is essentially that small remaining amounts of the porogen phase can be tolerated in the final porous substrate.

Blend Preparation, Solvent Extraction and Continuity of the Porogen Phase

Blend mixing of polymers A, B and compatibilizer in the molten state can be carried out by single-screw extrusion, twin-screw extrusion, or any classic melt mixing technology.

Extractions are generally performed in a Soxhlet extraction apparatus, followed by drying the resulting porous articles in a vacuum oven. Extraction is performed until the dried extracted articles achieved a constant weight. A gravimetric method is then used to calculate the extent of continuity of the porogen phase, using the simple equation:

% continuity of $P=(\text{weight } P_{initial} - \text{weight } P_{final})*100/\text{weight } P_{initial}$ wherein P corresponds to the porogen phase or to the porogen phase with half of the quantity of the compatibilizer. $P_{initial}$ corresponds to the weight of P in the blend before the extraction step, whereas $P_{final}$ corresponds to the weight of P remaining after extraction.

A fully continuous phase can be considered as one demonstrating a 100% continuity level. A highly continuous phase can be considered as one demonstrating a level of continuity between 50 and 100%. The onset of co-continuity can be defined as the minimum concentration at which a given phase becomes 100% continuous.

Controlling Process Parameters to Achieve Controlled Morphology of the Blend and/or of the Resulting Porous Article In a particular embodiment, annealing is used to substantially increase the phase size in the polymeric blend, and therefore the pore size of the porous article. The effects vary according to the annealing time, the annealing temperature and to the composition of the blend to be annealed. The optional annealing step occurs right after the melt blending step b), when the blend is still in the molten state, in the above process or after freezing-in the morphology in step c).

In a particular embodiment, the polymer blend in the molten state is shaped into various forms such as films, fibres, tubes, pins, plates, screws, or any other geometry that can be obtained using dies and moulds typical of classic polymer processing technology, such as extrusion and injection molding. Cooling then retains the desired form of the final porous article.

In another particular embodiment, the polymer blend, in the molten or solid state, is submitted to specific mechanical stresses that tend to orient the co-continuous polymer phases of A and B in one preferential direction. This processing enables to have an oriented porosity, or pores with a preferentially oriented form.

In another particular embodiment, the unextracted blend of polymers is etched for a few seconds in a common solvent for A and B to obtain an asymmetric, open-cell morphology in the final porous article.

In another particular embodiment, the porous article is quickly immersed in a solvent for its polymeric component A to obtain a closed-cell structure with a smooth, non-porous skin. Control of skin thickness can be achieved by modifying the time of immersion: an increase in the time of immersion results in a thicker non-porous skin. Chloroform can usually be used for this additional step.

Novel Microporous Articles:

The morphology of the microporous articles prepared in accordance with the method of the present invention was studied using three different methods: Scanning Electron Microscopy (SEM) combined with Image Analysis, Brunner-Emmett-Teller (BET) method and Mercury Intrusion Porosimetry (MIP).

SEM: The blended specimens were microtomed to create a perfect plane face using a Leica RM 2165 microtome equipped with a glass knife. After solvent extraction of the porogen phase and coating with a gold-palladium alloy, the microtomed specimens were observed under a JOEL JSM 840 Scanning Electron Microscope at a voltage of 10 or 5 kV. SEM is an adequate approach to measure the domain size and distribution of a dispersed phase. However, it is a lot less adequate to examine the microstructure in the region of co-continuity since this approach is based on a two-dimensional analysis, whereas co-continuity is a complex three-dimensional interpenetrating structure.

BET: A flowsorb BET instrument was used to measure the surface area of the extracted samples, and the number-average diameter ($d_o$) was obtained. The experimental error is ±4%.

MIP: A Poresizer was used to determine the volume-average pore diameter ($d_v$), the volume/surface ratio (V/S) and pore size distribution. Thereby, the number-average diameter $d_n$ can also be obtained from the volume/surface ratio ($d_n$=4V/S). The experimental data treatment is based on the Washburn equation:

$$Pr = -2\sigma \cos \theta,$$

where P is the applied pressure, r is the radius of the pore, $\sigma$ is the surface tension of the mercury and $\theta$ is the contact angle. The experimental error is ±5%.

The porous biodegradable polymeric article comprises an essentially continuous porosity with a void volume from 10 to 90%, its pore diameters show a unimodal distribution set to a predefined unimodal peak location corresponding to a chosen pore diameter, and wherein a majority of pores has a diameter within ±50% of the chosen pore diameter.

Distribution curves of microporous articles according to the invention are shown in FIGS. 13 to 16. It is shown in those figures that a high control of the parameters (mixing temperature, time, speed, annealing time and temperature, etc.) allows obtaining numerous chosen pore diameters for peak locations of the diameter unimodal distribution.

The fact that a majority of pores of an article according to the present invention has a diameter within ±50% of the chosen pore diameter also graphically appears on distribution curves as shown on FIGS. 13 to 16. Indeed, drawing two vertical lines at values of diameters d corresponding to:

$$d=d_v(\text{chosen pore diameter})+d_v*50\% \text{ and}$$

$$d=d_v-d_v*50\%,$$

allows verifying that the so defined area under the curve of incremental volume represents more than 50% of the total void volume.

A pore diameter up to 500 μm can be chosen for the predefined peak location of the unimodal distribution curve. Choices of a low viscosity of A (short chain polymer A), a high interfacial tension between A and B (A and B fully immiscible), and high time and temperature for annealing allow obtaining such microporous articles.

A pore diameter down to 20 nm can be chosen for the predefined peak location of the unimodal distribution curve. Choices of a high viscosity for A (long chain polymer A) and of a very low interfacial tension (with a compatibilizer or with B being a copolymer of A) allow obtaining such microporous articles.

In a preferred embodiment, the predefined unimodal peak location corresponds to a chosen pore diameter selected from 20 nm to 500 μm. In a more preferred embodiment, the predefined unimodal peak location corresponds to a chosen pore diameter selected from 1 to 72 μm.

In another preferred embodiment, the predefined unimodal peak location corresponds to a chosen pore diameter selected from 1 to 72 μm and the majority of pores has a diameter within ±40% of the chosen pore diameter.

In still another preferred embodiment, the predefined unimodal peak location corresponds to a chosen pore diameter selected from 1 to 3 μm, and wherein the majority of pores has a diameter within ±25% of the chosen pore diameter.

Microporous biodegradable articles of the present invention can of course be used in tissue engineering, as substrates for controlled release applications, or as implantable medical devices, when biocompatible.

Although the present invention has been described hereinabove by way of preferred embodiments thereof, it can be modified, without departing from the spirit and nature of the subject invention as defined in the appended claims.

Example 1

Method of Preparing Microporous Poly(L-Lactide) (PLLA) Articles from Poly(L-Lactide)/Polystyrene (PLLA/PS) Compatibilized and Non-Compatibilized Blends The compatibilizer used was a copolymer of PLLA and PS. Binary blends and compatibilized ternary blends were prepared by melt mixing the polymers and copolymer in a Brabender internal mixer with roller blades, under a constant high flow of dry nitrogen. Dry nitrogen is required to avoid a dramatic melt degradation of the PLLA. Prior to blending, PLLA and PS were dried for 48 hrs in a vacuum oven at 70° C. PLLA and PS were added simultaneously in the mixing chamber and the compatibilizer, when used, was introduced immediately after. The mixing blades were maintained at 50 rpm and the temperature was set at 200° C. All the blend concentrations are reported in the figures as volume fraction, except the compatibilizer concentration, which is presented as a weight-percentage value based on the polystyrene phase.

Cyclohexane extraction of the polystyrene phase was performed at about 50 to 60° C. in a Soxhlet extraction apparatus. After the extraction time, the specimens were then dried in a vacuum oven for at least 10 hours at 50° C.

Example 2

Continuity Development of the PS Phase in Non-Compatibilized and Compatibilized PLLA/PS Blends Non-compatibilized and compatibilized PLLA/PS blends were used to prepare PLLA microporous articles as described in example 1. The continuity of the PS phase, that is to say of the void space after extraction, was calculated using the above-described gravimetric method, and the results are shown in FIG. 1.

Figure 2:
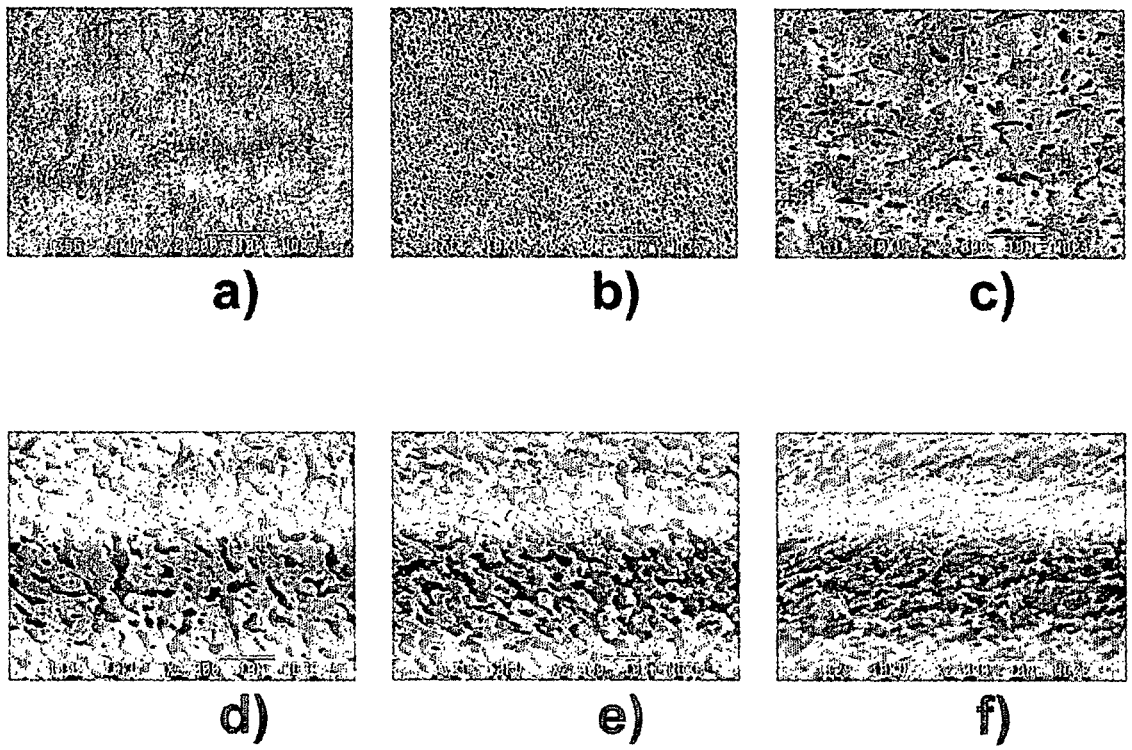
FIG. 2 is a Scanning Electron Micrograph (SEM) of PLLA/PS blends for various compositions (PS extracted from the samples): a) 90/10, b) 80/20, c) 70/30, d) 60/40, e) 35/65, and f) 25/75. The white bar indicates 10 microns.

For the binary PLLA/PS blends (white circles), the plateau indicating maximum continuity of the PS phase is achieved at about 45% PS. In this case, the porosity is between 43 to 75% and the number-average pore diameter is between 1.5 and 2.5 µm. It is interesting to note that the PLLA/PS blend maintains structural integrity up until 75-80%, at which concentration the extracted samples disintegrate. The SEM micrographs shown in FIG. 2 illustrate the porous microstructure at various concentrations of PS.

Figure 3:
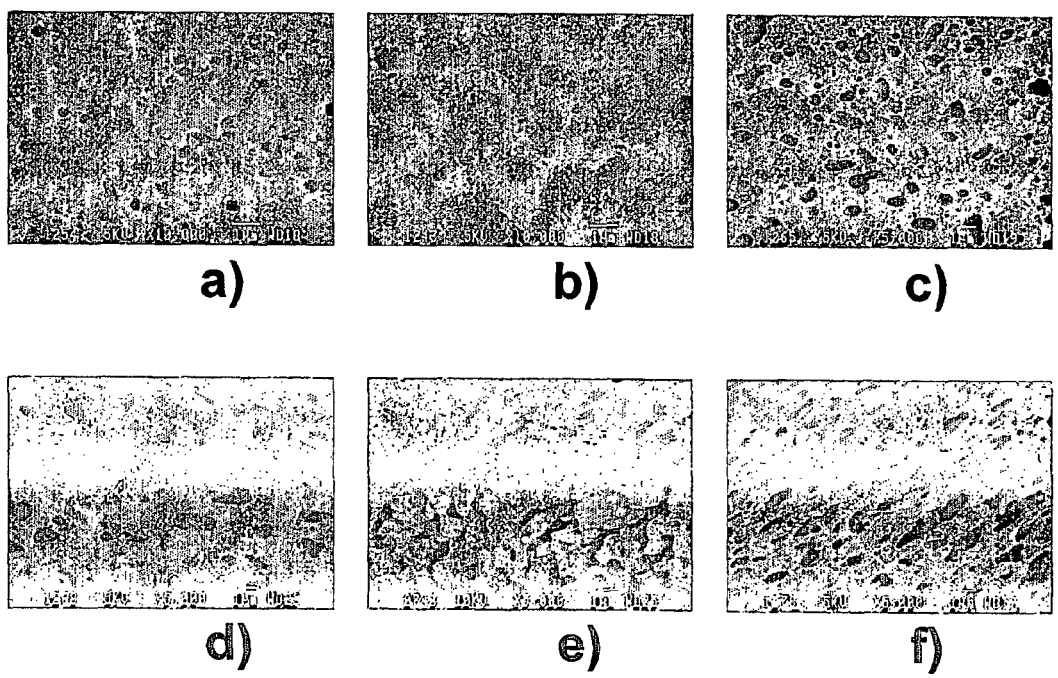
FIG. 3 is a SEM of PLLA/PS/copolymer blends for various compositions (PS/extracted from the samples): a) 90/10, b) 80/20, c) 70/30, d) 60/40, e) 50/50, and f) 40/60. The white bar indicates 1 micron.

FIG. 1 also shows the effect of the PLLA/PS copolymer on PS continuity development (black circles). 12% of copolymer based on the weight of the PS phase was used for each blend over the range of compositions studied. Micrographs of these structures are shown in FIG. 3. It is interesting to note that no effect of the copolymer is observed on the onset of co-continuity for the blend. However, the disintegration point for the compatibilized blend occurs here at about 60-65% PS. This shift indicates that the diblock copolymer is effective for PLLA in PS blends and not when the proportions are inversed.

Example 3

Effect of the Compatibilization on the Pore Size and Pore Size Distribution

Figure 4:
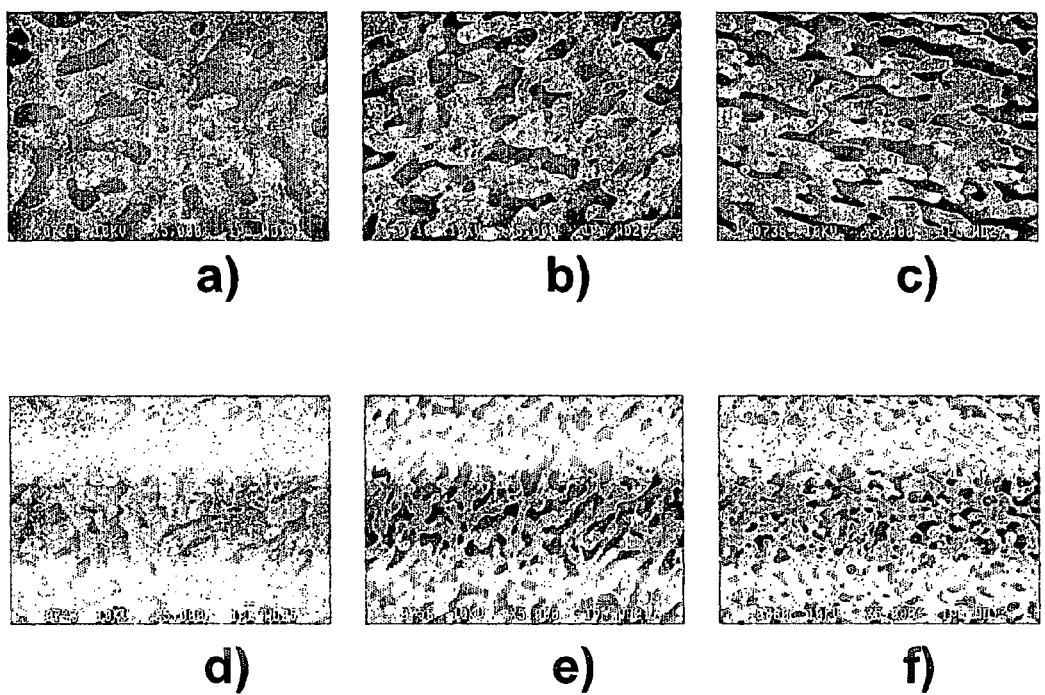
FIG. 4 is an SEM showing action of the diblock copolymer to reduce the pore size for the blend PLLA/PS 50/50 at the copolymer concentrations of a) 2.5%, b) 5%, c) 8%, d) 12%, e) 15%, and f) 20%. The white bar indicates 1 micron.

Non-compatibilized and compatibilized PLLA/PS blends were used to prepare PLLA microporous articles as described in example 1. Micrographs in FIG. 4 illustrate the use of increasing concentrations of diblock PLLA/PS copolymer on the resulting article pore size. A significant reduction is observed. In a PLLA/PS (50/50) blend, the number-average pore diameter can be decreased to 0.6-0.8 microns and the volume-average pore diameter is lower than 1 micron in the presence of a compatibilizer.

Figure 5:
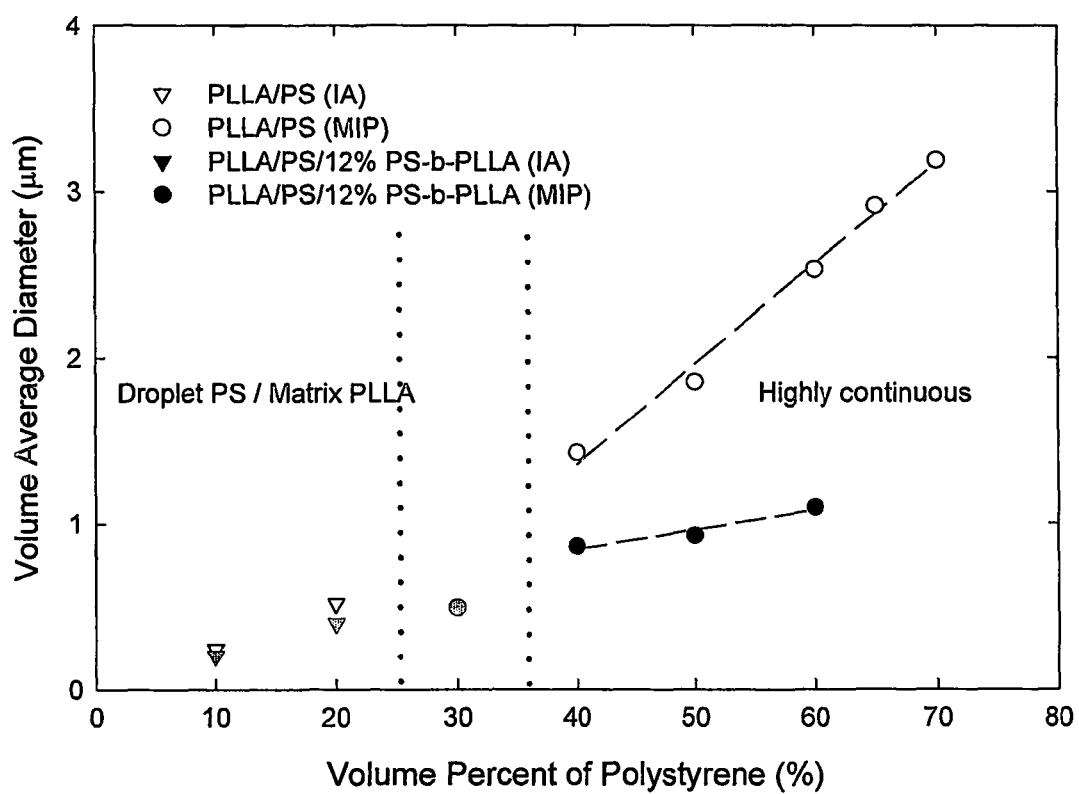
FIG. 5 is a diagram showing the volume average pore diameter as a function of PS volume fraction for both compatibilized and non-compatibilized blends, as measured by image analysis and Mercury Intrusion Porosimetry (MIP) technique.

FIG. 5 shows the volume average pore diameter as a function of PS volume fraction for both compatibilized and non-compatibilized blends. The number average diameter results (not shown) show similar trends. PLLA/PS blends with a highly continuous PS phase from 40 to 70% PS clearly demonstrate a significant increase in pore diameter with volume fraction. This behaviour is typical for an immiscible binary blend system in which continuity development is dominated by droplet-droplet coalescence. Adding a compatibilizer has little influence on the microstructure up to a PS concentration of 40%, and leads to only a slight change from 40 to 60% PS. In such ternary blends, continuity development is also dominated by droplet-droplet interactions, but dynamic coalescence is dramatically reduced because of the presence of the compatibilizer. For the blends with 50 and 60% PS, the compatibilizer reduces the pore size significantly.

Figure 6:
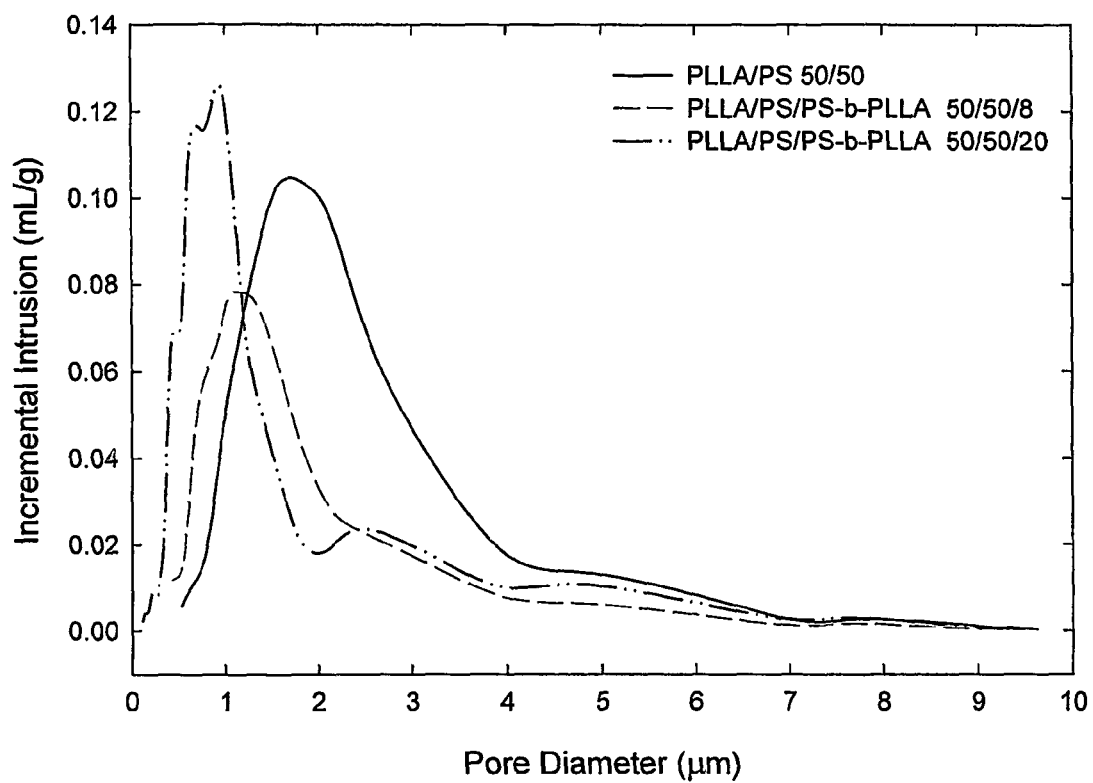
FIG. 6 is a diagram showing the effect of the compatibilizer on the unimodal pore size distribution as measured by MIP, on extracted samples.

FIG. 6 shows that the compatibilizer also significantly reduces the pore size distribution of the microporous article. The distribution indeed remains unimodal, but at 20% diblock (of the PS phase weight), the pore diameters are essentially distributed in a range of less than 3 µm, which is characteristic of all the microstructures obtained in the present invention from compatibilized blends.

Example 4

Effect of Static Annealing on Compatibilized and Non-Compatibilized Blends

Figure 7:
FIG. 7 is a SEM showing the effect of static annealing at 200° C. for 90 min on the PLLA/PS/compatibilizer blends (PS extracted from the samples), at the following concentrations: a) 50/50/0, b) 50/50/2.5, and c) 50/50/20. The white bar indicates 10 microns.
Figure 7:
Figure 7:
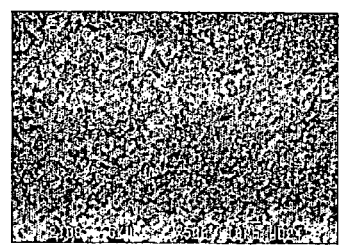
Figure 8:
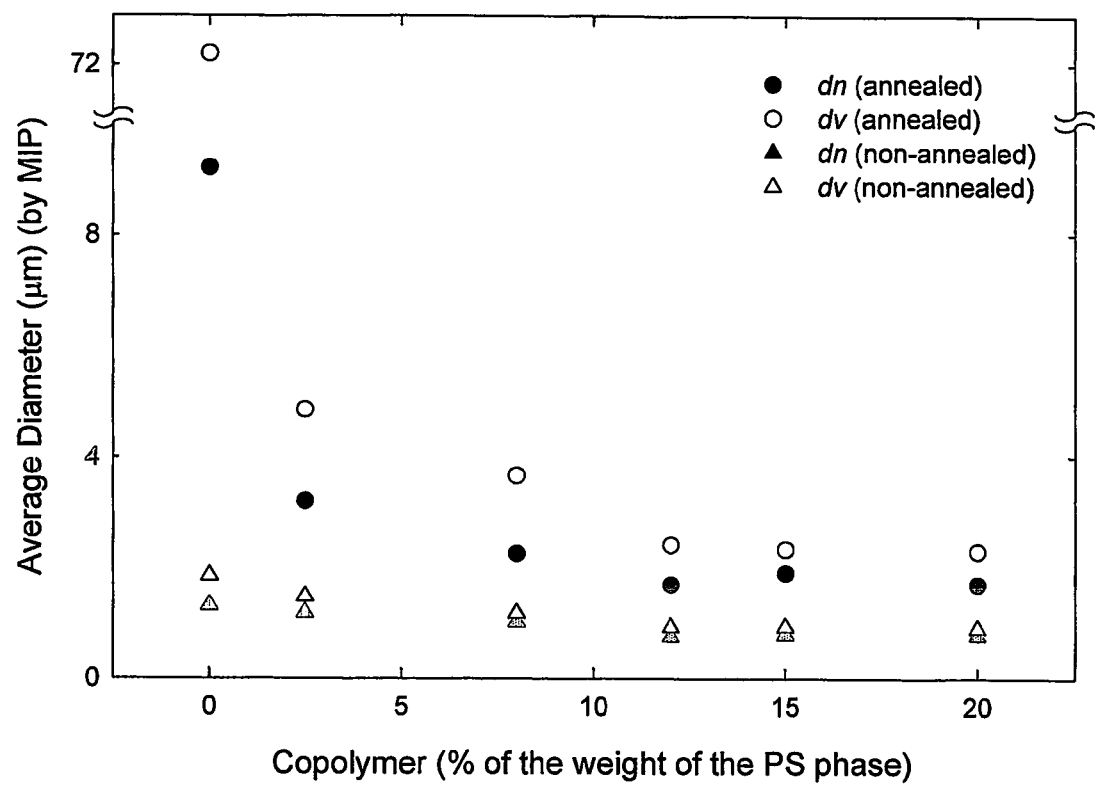
FIG. 8 is a diagram showing a comparison of the average diameters for PLLA/PS/diblock 50/50/x, measured by MIP for both annealed (90 min at 200° C.) and non annealed samples (PS extracted from the samples prior to MIP measurement)

Non-compatibilized and compatibilized PLLA/PS blends were used to prepare PLLA microporous articles as described in example 1, and some of the samples were annealed right after the melt blending at 200° C. for 90 min. FIG. 7 illustrates the effect of static annealing on the 50/50 blend system. It is clear that both the time at temperature and the presence of a compatibilizer have a profound effect on the microstructure of the material under these conditions. The pore diameters, measured after solvent extraction of the above blends, are reported in FIG. 8.

The pore size increases dramatically with the annealing of the 50/50/0 blend, from 1.3 to 9.2 µm ($d_n$) and from 1.9 to 72.2 µm ($d_v$). Addition of 2.5% of the diblock copolymer acts to considerably reduce the coalescence, and the increase in diameter with annealing is therefore lower. In that case, $d_n$ increases from 1.2 to 3.2 µm and $d_v$ increases from 1.5 to 4.8 µm after annealing. For 20% of copolymer, $d_n$ increases from 0.8 to 1.7 µm and $d_v$ increases from 0.9 to 2.3 µm. In compatibilized blends, it is observed that the pore diameter also increases with annealing time.

It is important to note that after annealing, the PS continuity in the 50/50 blend is slightly reduced by 3% and that increasing the copolymer content leads to a higher continuity of the same blend after annealing.

Example 5

Some Microporous Structures Obtained with Various Polymer Blends

TABLE 1

Summary a few examples of porous articles and polymer blends used.

| Polymer A (porous article) | Polymer B to be extracted |
|---|---|
| PGA | PLLA |
| PLLA | PS |
| PLLA | PCL |
| PLLA | PEO |
| PLLA | PGA |
| PCL | PS |
| PCL | PEO |
| PCL | PDLLA |
| PDLLA | PS |
| PDLLA | PEO |

Example 6

Manufacture of Porous Polymeric Capsules by Compression Molding, and Modification of the Surface Properties (Skin)

Although the figures referred to in this example have been obtained from porous articles resulting from non-compatibilized blends, it is to be understood that the results perfectly apply to articles resulting from compatibilized blends.

Figure 9:
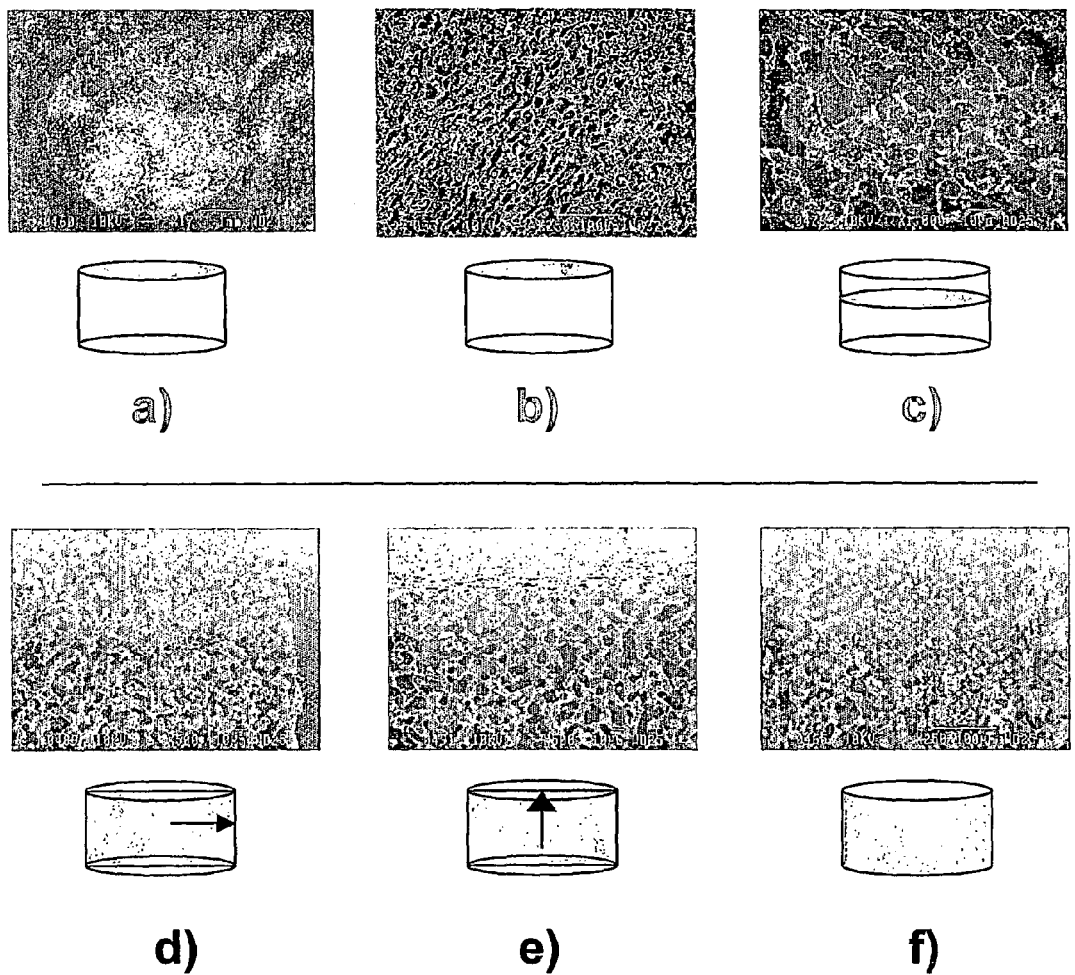
FIG. 9 shows scanning electron micrographs of porous open-cell PLLA cylinders (diameter: 5 mm, height: 3 mm) obtained from the blend PLLA/PS (35/65) after internal mixing followed by compression molding, and then the selective extraction of the PS phase. The white bar indicates a) 1 mm; b) 100 microns; c) 10 microns; d) 10 microns; e) 10 microns; f) 100 microns.

FIG. 9 presents PLLA porous open-cell capsules (diameter: 5 mm, height: 3 mm) obtained from the blend PLLA/PS (35/65) after internal mixing followed by compression molding and then selective extraction of the PS phase. The void volume (porosity) is about 62-64% and the volume-average pore diameter is about 4 microns.

Figure 10:
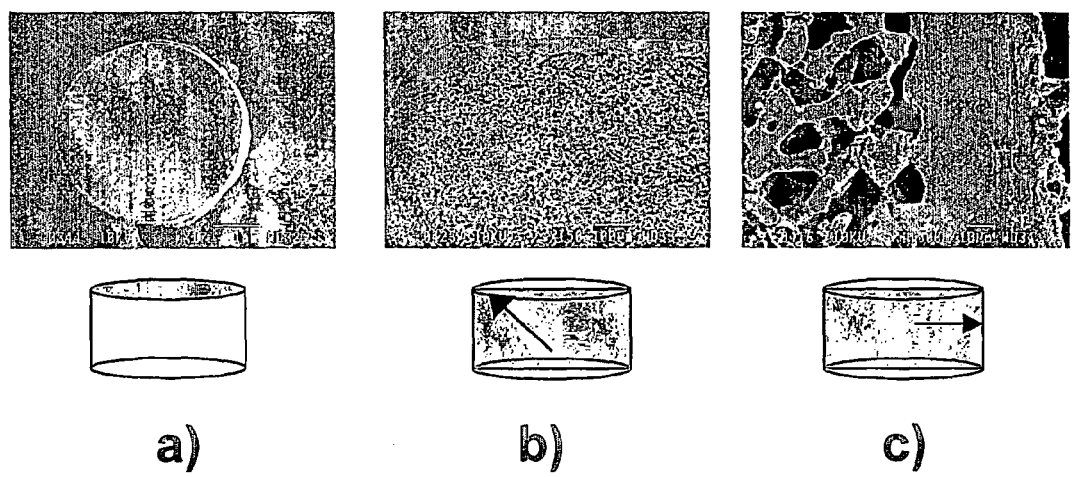
FIG. 10 shows scanning electron micrographs (various magnifications) of porous closed-cell PLLA cylinders (diameter: 5 mm, height: 3 mm) obtained from the blend PLLA/PS (35/65) after internal mixing followed by compression molding, selective extraction of the PS phase and then by a brief immersion in a solvent for PLLA. The white bar indicates a) 1 mm; b) 100 microns; c) 10 microns.

FIG. 10 presents the same porous capsules, after a brief immersion in a solvent for PLLA. It results in a closed-cell skin surrounding the microporous structure. The solvent and the soaking time allow controlling the thickness of the closed-cell wall.

Figure 11:
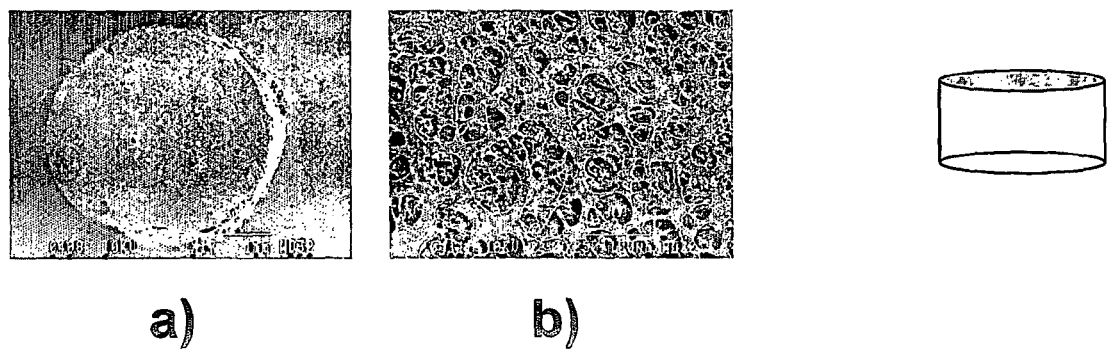
FIG. 11 shows scanning electron micrographs (different magnifications) of porous PLLA cylinders with a peculiar porous skin (diameter: 5 mm, height: 3 mm) obtained from the blend PLLA/PS (35/65) after internal mixing followed by compression molding, a brief immersion in a common solvent for PLLA and PS and then by the selective extraction of the PS phase. The white bar indicates a) 1 mm; b) 100 microns.

FIG. 11 presents capsules coming from the blends used previously, but this time the brief immersion is carried out in a common solvent for PLLA and PS, before the extraction of the PS phase. It results in a peculiar porous skin (large holes at the surface), and therefore in an asymmetrical morphology of the capsule.

Example 7

Water Penetration and Loading with Model Drug Compound

Porous PLLA was tested for water uptake and BSA (Bovine Serum Albumin) to show the advantage of highly controlled pore sizes in the area of controlled release applications. Although the figures referred to in this example have been obtained from porous articles resulting from non-compatibilized blends, it is to be understood that the results perfectly apply to articles resulting from compatibilized blends.

Binary biodegradable blends of polycaprolactone (PCL) and PLLA were prepared and the PCL extracted according to the method presented in example 1 with PLLA/PS blends. Porous samples used for water penetration and loading experiments were washed in ethanol and then dried. Water penetration was measured by immerging porous capsules (of cylinder shape) in distilled water at both atmospheric and high pressure in a controlled pressure apparatus. At different time, the capsules were removed from their vials, their lateral surface was dried and they were then weighed. Their intrusion volume of water expressed as ml per g of dry polymer was calculated from the difference between the wet and the dry initial weights. Then the fraction of the porosity (%) filled with water was obtained from the ratio with the maximum theoretical intrusion volume. Triplicates were run for each group.

Figure 12:
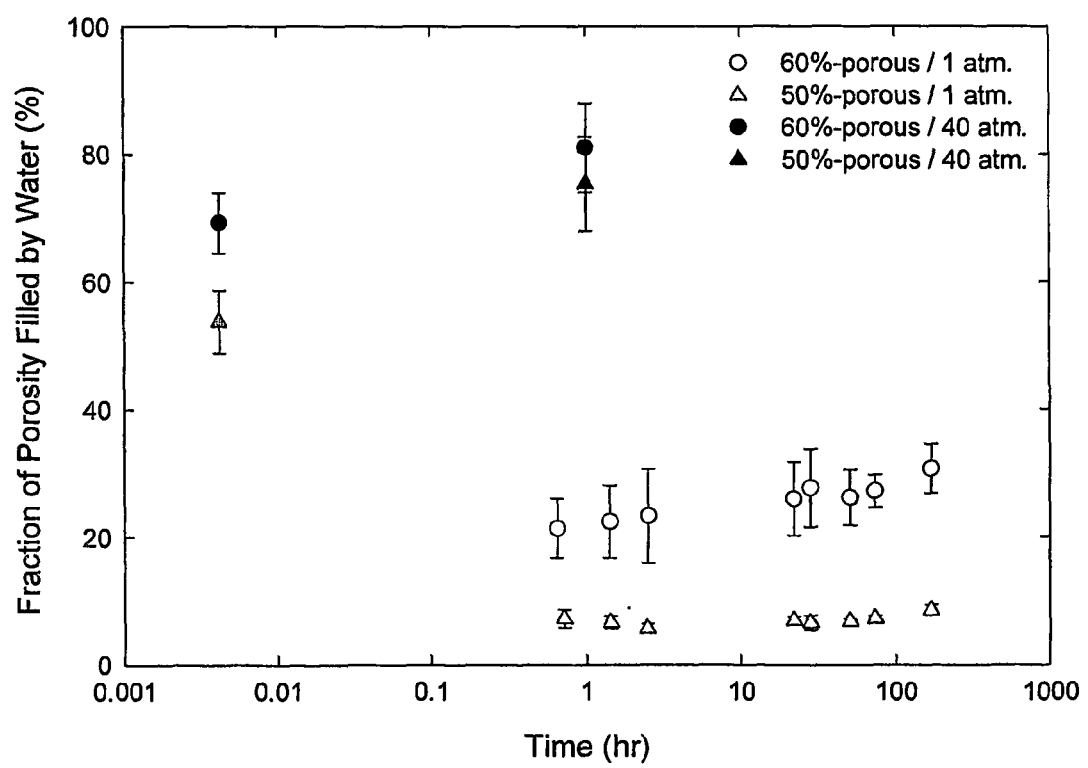
FIG. 12 is a diagram showing the fraction of the pores filled with water at atmospheric pressure and 40 atm, after immersion in distilled water.
Figure 13:
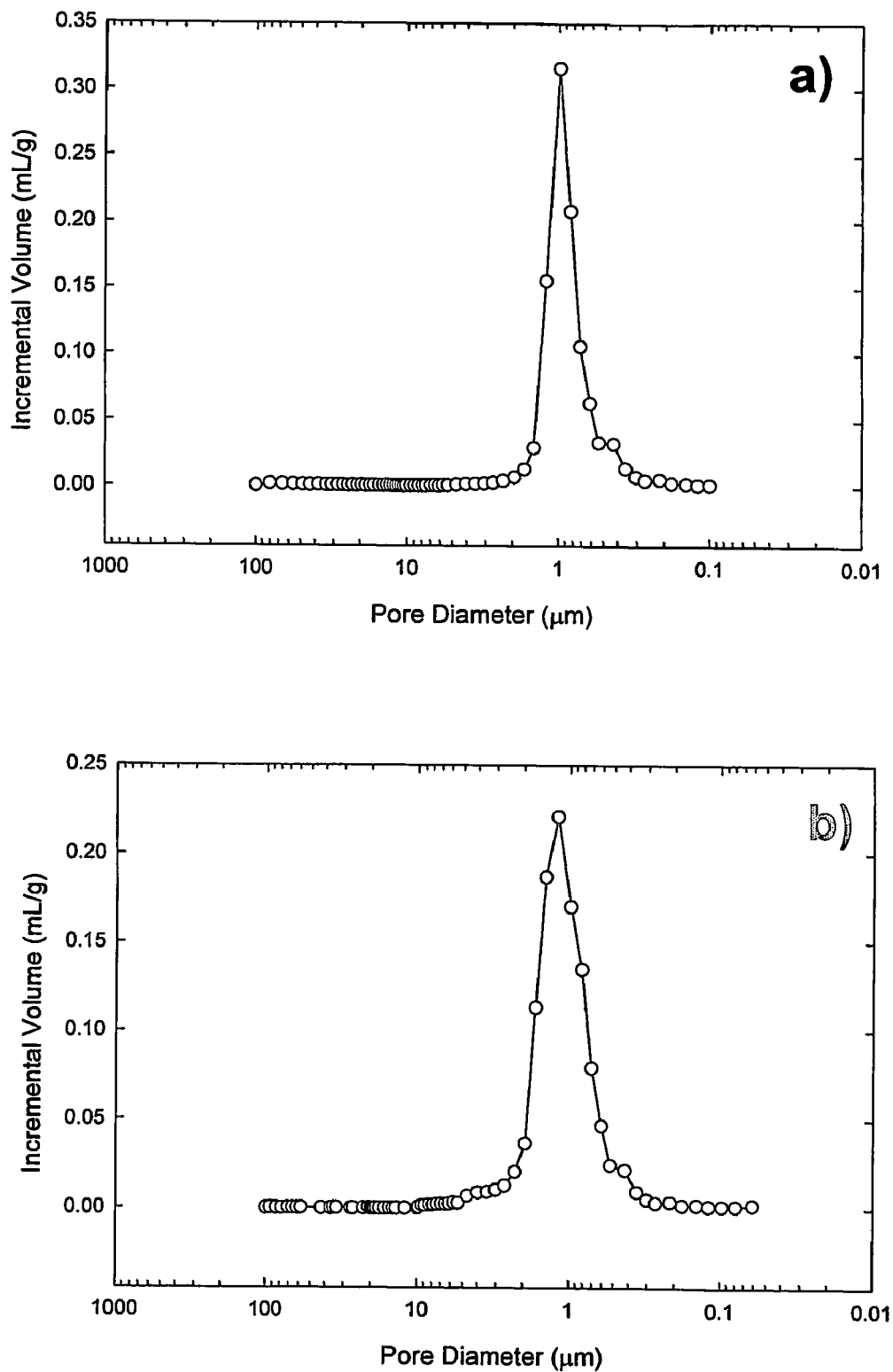
FIG. 13 is a diagram showing the unimodal distribution of the pore diameters for a microporous PCL article obtained from a PCL/PS blend in different conditions: a) mixing at 140° C., 4 min, 50 rpm ($d_v$=1.0 µm, void volume=50%); b) mixing at 140° C., 5 min, 50 rpm ($d_v$=1.3 µm, void volume=50%), as measured by MIP.
Figure 14:
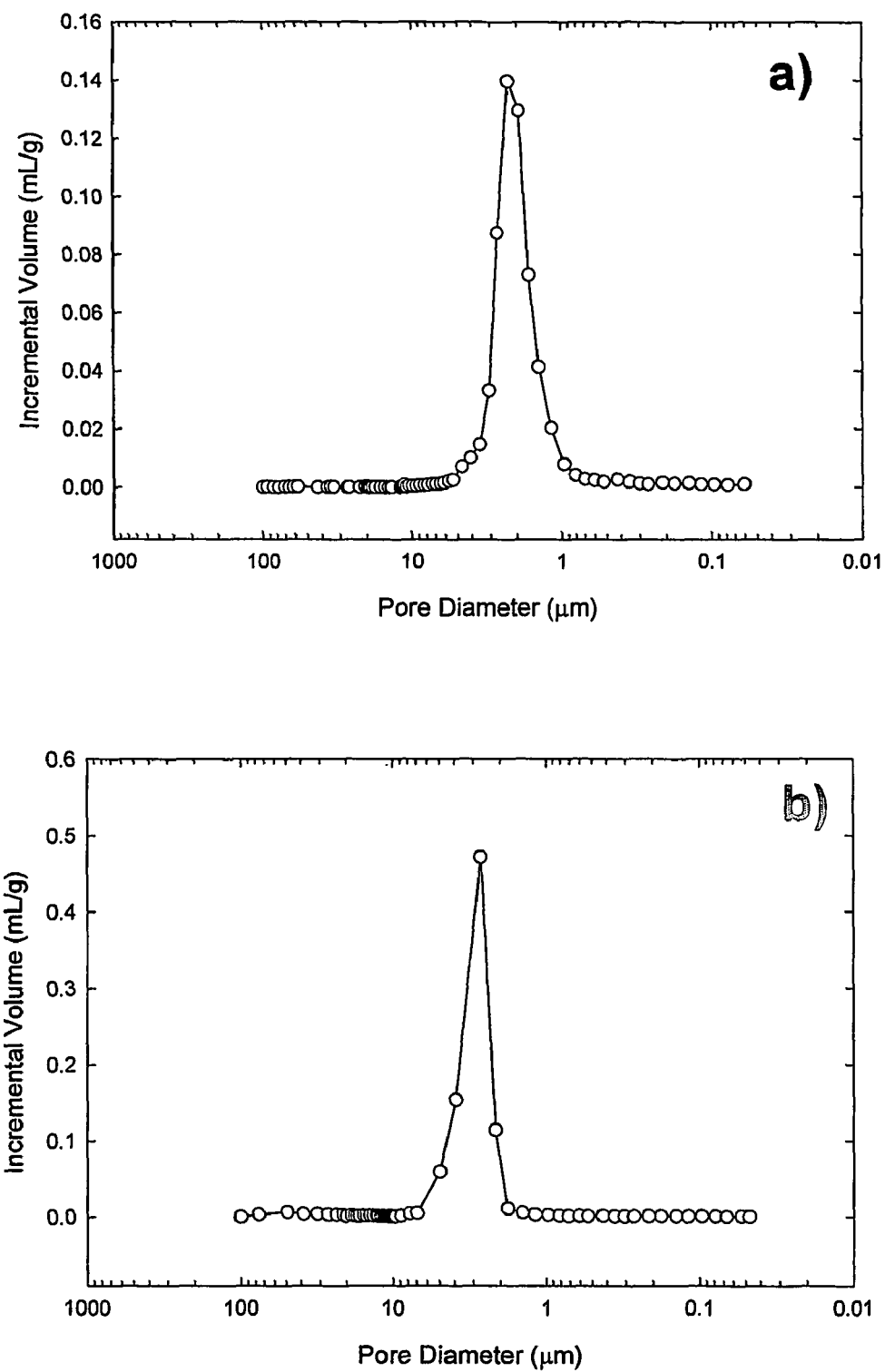
FIG. 14 is a diagram showing the unimodal distribution of the pore diameters for a microporous PLLA article obtained from a PLLA/PS/copolymer blend in different conditions: a) mixing at 200° C., 7 min, 50 rpm, annealing at 200° C., 90 min ($d_v$=2.3 µm, void volume=50%); b) mixing at 200° C., 5 min, 50 rpm, annealing at 220° C., 60 min ($d_v$=3.3 µm, void volume=50%), as measured by MIP.
Figure 15:
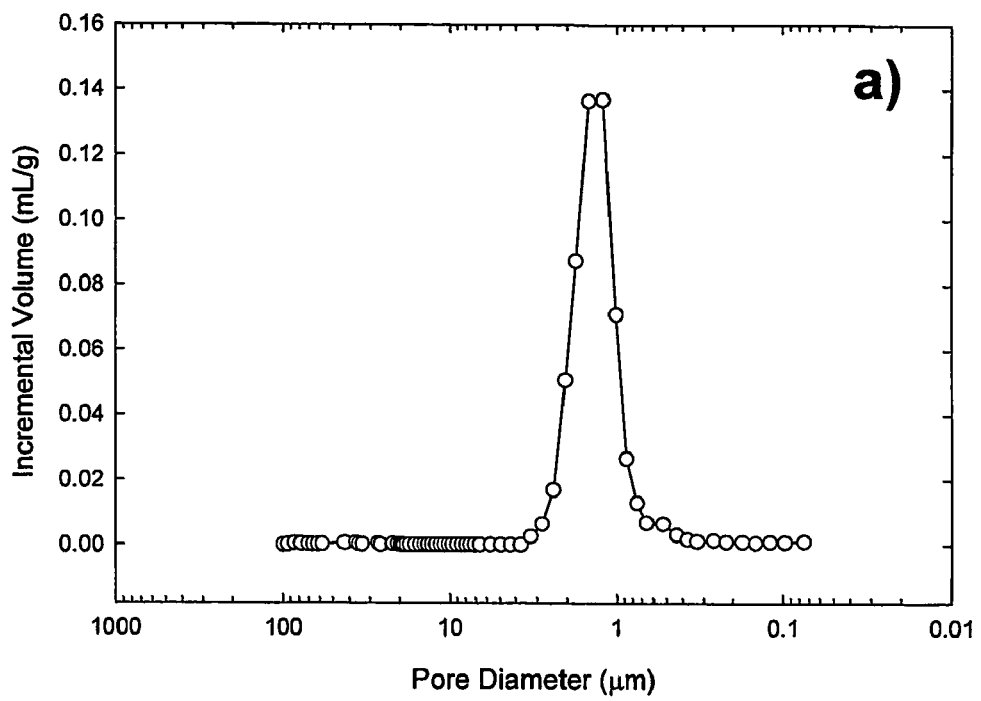
FIG. 15 is a diagram showing the unimodal distribution of the pore diameters for microporous articles obtained in different conditions: a) microporous PLLA obtained from PLLA/PCL blend, mixing at 200° C., 5 min, 50 rpm ($d_v$=1.5 µm, void volume=50%); b) microporous PCL obtained from PCL/PS blend, mixing at 230° C., 5 min, 50 rpm ($d_v$=11.8 µm, void volume=50%), as measured by MIP.
Figure 15:
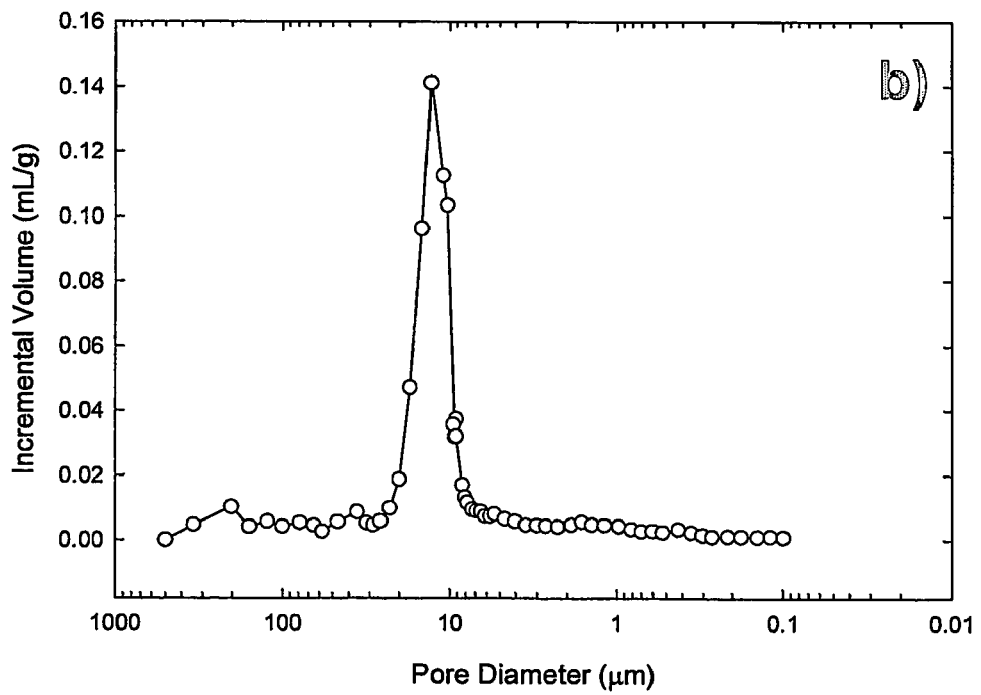
Figure 16:
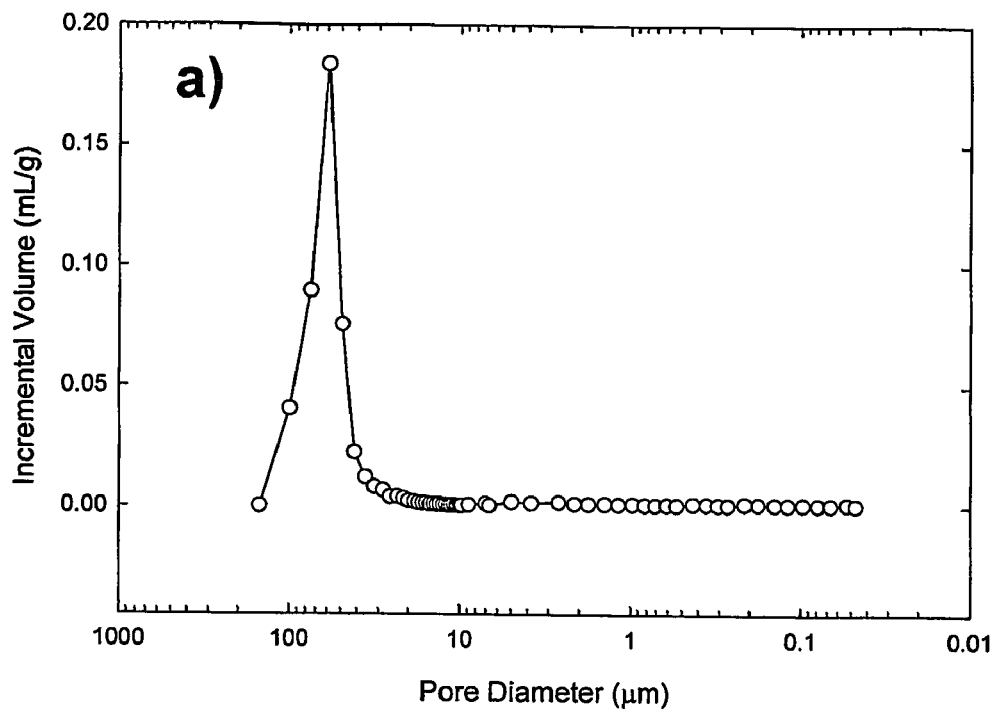
FIG. 16 is a diagram showing the unimodal distribution of the pore diameters for a microporous PLLA article obtained from a PLLA/PS blend in different conditions: a) mixing at 200° C., 5 min, 50 rpm, annealing at 220° C., 60 min (dv=64.3 µm, void volume=50%); b) mixing at 200° C., 7 min, 50 rpm, annealing at 200° C., 90 min ($d_v$=72.2 µm, void volume=50%), as measured by MIP.
Figure 16:
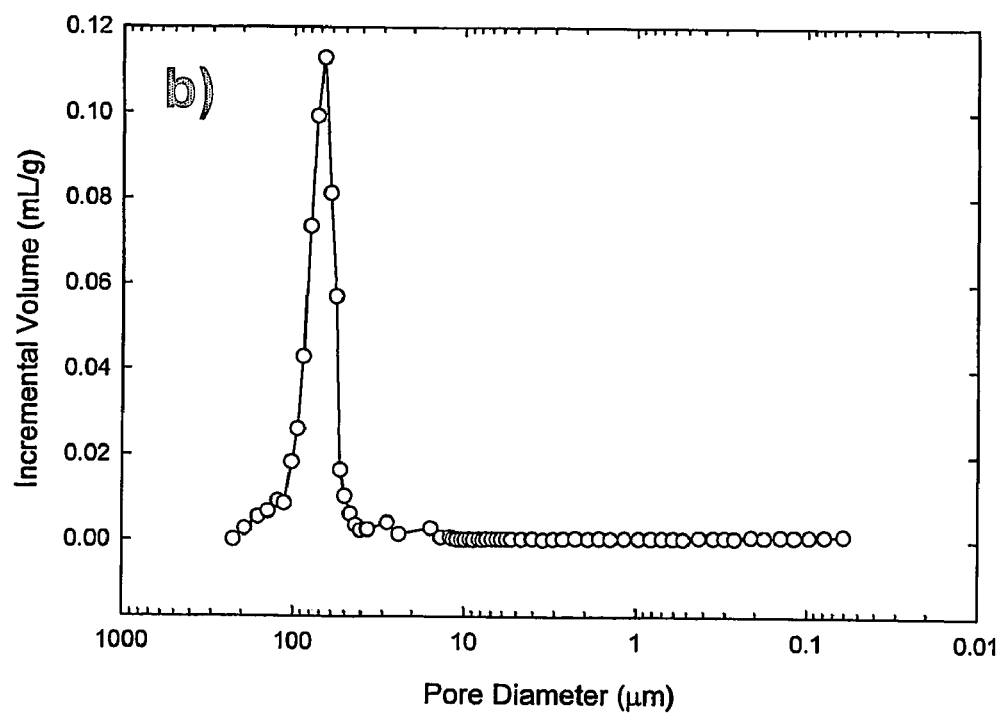

The water penetration study was carried out on 50% and 60%-porous cylinders from blends annealed for 4 h, with volume average pores diameters of 37 and 72 µm respectively, and the results are shown in FIG. 12. The water penetration is low at atmospheric pressure and the cylinders float at the surface of the glass tubes. Only 8.5% and 30.6% of the porosity were filled by water for 50% and 60%-porous cylinders, respectively after 7 days of immersion. The use of the high-pressure apparatus at 40 atm for 15 s results in water filling 54% and 70% of the available porosity, respectively. After 1 h, the water filled 75% and 81% of the available porosity, respectively. This experiment with PLLA articles having large average pore sizes only aimed at demonstrating that the internal porous structure is accessible to aqueous solution.

Another experiment was conducted on porous PLLA capsules (in cylinder shape) having 50% void volume and an average volume diameter of 1.5 µm. They were loaded with BSA (from Sigma, A-6003) as a model drug compound. The capsules were immersed in a concentrated solution of BSA (250 mg·ml$^{-1}$) and placed in the controlled pressure apparatus especially developed for this purpose. This apparatus enables to apply a controlled nitrogen pressure, a vacuum or to inject the BSA solution after degassing the porous material. Pressures of 40, 2.5, 1 and 0.18 atmospheres were maintained for times varying from 15 min to 24 h. The amount of BSA loaded in the porous material was determined by gravimetry after driving off water as follows:

$$\text{Encapsulation} = (Mf - Mi)/Mi$$

where Mi is the weight of the porous cylinder before loading and Mf is the weight of the dried polymer cylinder after loading.

The results are shown in Table 2 below. A variety of pressure and time at pressure conditions were studied and it was found that the highest loading of BSA was obtained when an initial vacuum was applied followed by 30 min at 40 atm pressure. Under that latter condition it was possible to obtain a high BSA loading value of 0.235 (weight BSA/weight of dry capsule). Thus, high quantities of a model drug can be made to enter the porous structure. This result and that of the accessibility of aqueous solution to the porous volume in the PLLA clearly show the enormous potential of the porous material prepared according to the method of the present invention in controlled release applications.

TABLE 2

Loading of the porous materials on 50%-porous material (dv = 1.5 μm)

| Conditions | Step 0 1 atm. | Step 1 0.18 atm (vacuum) | Step 2 2.5 atm | Step 3 40 atm | Encapsulation (%) |
|---|---|---|---|---|---|
| A | 24 to 168 h | — | — | — | ~0 |
| B | — | 1.75 h | — | — | 11.5 |
| C | — | — | 0.5 h | — | 13.8 |
| D | — | 1.75 h | 24 h | — | 17.1 |
| E | — | — | — | 24 h | 18.8 |
| F | — | 1.75 h | — | 24 h | 19.8 |
| G | — | — | — | 1 h | 20.3 |
| H | — | 1.75 h | — | 0.5 h | 23.5 |

What is claimed is:

1. A microporous polymeric article having a target pore diameter $d_v$, comprising an essentially continuous porosity with a controlled void volume from 10 to 90%, wherein pore diameters show a unimodal distribution set at a predefined unimodal peak location corresponding to said target pore diameter $d_v$, and wherein a majority of pores have a diameter d of at least $d_v-50\%$ and at most $d_v+50\%$, prepared according to a method comprising the steps of:
   a) determining a target pore diameter $d_v$;
   b) selecting at least one polymer A and at least one polymer B at least partially immiscible with A, according to the target pore diameter $d_v$ determined in step a);
   c) melt blending the selected polymers from step b), thereby preparing a polymer blend, wherein said polymers A and B have an essentially continuous morphology;
   d) cooling said polymer blend to room temperature, thereby retaining its morphology; and
   e) extracting said polymer B, at least partially, from the polymer blend by dissolving said polymer B in a solvent that is a non-solvent of polymer A.

2. The microporous polymeric article according to claim 1, wherein the target pore diameter $d_v$ is from 20 nm to 500 μm.

3. The microporous polymeric article according to claim 2, wherein the target pore diameter $d_v$ is from 1 to 72 μm.

4. The microporous polymeric article according to claim 3, wherein the majority of pores have a diameter d comprised in a range between $d_v-40\%$ and $d_v+40\%$.

5. The microporous polymeric article according to claim 1, wherein the target pore diameter $d_v$ is from 1 to 3 μm, and wherein the majority of pores have a diameter d comprised in a range between $d_v-25\%$ and $d_v+25\%$.

6. The microporous biodegradable polymeric article according to claim 1, wherein the porosity is fully continuous.

7. The microporous biodegradable polymeric article according to claim 1, wherein the article has a symmetric morphology.

8. The microporous biodegradable polymeric article according to claim 1, wherein the article has an asymmetric morphology.

9. The microporous biodegradable polymeric article according to claim 8, wherein the article has a closed-cell skin.

10. The microporous biodegradable polymeric article according to claim 1, wherein at least 95% of said article is made of a biodegradable medical polymer selected from the group consisting of poly(lactic acid), poly(glycolic acid), poly(lactic-co-glycolic), polyorthoesters, polycaprolactones, polyanhydrides and their copolymers.

11. The microporous biodegradable polymeric article according to claim 1, wherein at least 99% of said article is made of a biodegradable medical polymer selected from the group consisting of poly(lactic acid), poly(glycolic acid), poly(lactic-co-glycolic), polyorthoesters, polycaprolactones, polyanhydrides and their copolymers.

12. The microporous biodegradable polymeric article according to claim 1, wherein said article is essentially made of a biocompatible, implantable polymer.

13. A method of preparation of a microporous biodegradable polymeric article, comprising the steps:
   a) selecting at least one biodegradable polymer A, one polymer B, biodegradable or not, at least partially immiscible with A, and a polymeric compatibilizer C for A and B;
   b) melt blending the selected polymers from step a) and the compatibilizer C, thereby preparing a compatibilized polymer blend, wherein said polymers A and B have an essentially continuous morphology;
   c) cooling said polymer blend to room temperature, thereby retaining its morphology; and
   d) extracting said polymer B and said compatibilizer C, at least partially, from the polymer blend by dissolving them in a solvent that is a non-solvent of polymer A,
wherein said polymeric article has an essentially continuous porosity with a void volume from 10 to 90%, wherein pore diameters show a unimodal distribution set to a predefined unimodal peak location corresponding to a chosen pore diameter, and wherein a majority of pore has a diameter within ±50% of the chosen pore diameter.

14. The method according to claim 13, wherein said polymer A is a biodegradable medical polymer.

15. The method according to claim 14, wherein said polymer A is an aliphatic polyester.

16. The method according to claim 14, wherein said polymer A is selected from the group consisting of poly(lactic acid), poly(glycolic acid), poly(lactic-co-glycolic), poly(hydroxyalkanoates), polyorthoesters, polycaprolactones, polydioxanone, polyan hydrides and their copolymers.

17. The method according to claim 13, wherein said polymer B is a non-biodegradable polymer.

18. The method according to claim 13, wherein said polymer B is a biodegradable medical polymer.

19. The method according to claim 18, wherein said polymer B is selected from a group consisting of poly(lactic acid), poly(glycolic acid), poly(lactic-co-glycolic), poly(hydroxyalkanoates), polyorthoesters, polycaprolactones, polyanhydrides and their copolymers.

20. The method according to claim 13, wherein said compatibilizer C is a polymeric compatibilizer.

21. The method according to claim 20, wherein said compatibilizer C is a copolymer of A and B.

22. The method according to claim 13, wherein said polymers A and B are fully immiscible.

23. The method according to claim 13, wherein said polymer blend is co-continuous at more than 90%.

24. The method according to claim 13, wherein said polymer blend may contain one or more additives.

25. The method according to claim 13, wherein said polymer blend is submitted to a further step of controlled annealing between steps b) and c), thereby increasing the pore size of the porous article.

26. The method according to claim 13, wherein said polymer blend is submitted to controlled cooling rates in step c).

27. The method according to claim 13, wherein said polymer blend is further shaped into a geometrical form between steps b) and c).

28. The method according to claim 27, wherein said polymer blend is further shaped in a mold or die, between steps b) and c).

29. The method according to claim 27, wherein said polymer blend is shaped by injection molding, between steps b) and c).

30. The method according to claim 27, wherein said polymer blend is formed by extrusion, between steps b) and c).

31. The method according to claim 27, wherein said polymer blend is formed by melt spinning between steps b) and c).

32. The method according to claim 13, wherein said polymer blend is submitted to a mechanical stress that orients the porosity in at least one specific direction, between steps b) and c).

33. The method according to claim 13, wherein said polymer blend is submitted to a mechanical stress that orients the porosity in at least one specific direction, during step c).

34. The method according to claim 13, wherein said polymeric article is further submitted to a controlled immersion in a solvent for its polymer A after step d), thereby creating a closed-cell skin.

35. The method according to claim 13, wherein said polymer blend is further submitted to a controlled immersion in a common solvent for A and B between steps c) and d), thereby creating an asymmetric open-cell morphology in the porous article.

36. A method of tissue engineering utilizing a microporous article according to any one of claims 2 to 5 and 1.

37. The microporous biodegradable article obtained by the method according to any of claims 13-35, wherein said microporous biodegradable article is tissue engineering article.

38. A method of controlled release utilizing a microporous article according to any one of claims 2 to 5 and 1 as a substrate.

39. The microporous biodegradable article obtained by the method according to any of claims 13-35, wherein said microporous biodegradable article is a substrate for controlled release applications.

40. A method of forming an implantable medical device utilizing a microporous article according to any one of claims 2 to 5 and 1.

41. The microporous biodegradable article obtained by the method according to any of claims 13-35, wherein said microporous biodegradable article is an implantable medical device.

42. The microporous polymeric article according to any one of claims 2 to 5, said article being biodegradable.

43. The microporous polymeric article according to claim 1, wherein step b) further comprises selecting a polymeric compatibilizer C for A and B; step c) comprises melt blending the selected polymers from step a) and the compatibilizer C, thereby preparing a compatibilized polymer blend; and step e) comprises extracting said polymer B and said compatibilizer C, at least partially, from the polymer blend by dissolving them in a solvent that is a non-solvent of polymer A.

* * * * *